US009909956B1

(12) United States Patent
St Amant, III

(10) Patent No.: US 9,909,956 B1
(45) Date of Patent: Mar. 6, 2018

(54) CYCLONIC SYSTEM FOR ENHANCED SEPARATION OF FLUID SAMPLES AND THE LIKE, AND METHOD THEREFORE

(71) Applicant: Mayeaux Holding LLC, Gonzales, LA (US)

(72) Inventor: Valmond Joseph St Amant, III, St Amant, LA (US)

(73) Assignee: Mayeaux Holding LLC, Gonzales, LA (US)

( * ) Notice: Subject to any disclaimer, the term of this patent is extended or adjusted under 35 U.S.C. 154(b) by 105 days.

(21) Appl. No.: 14/953,725

(22) Filed: Nov. 30, 2015

Related U.S. Application Data

(60) Provisional application No. 62/087,067, filed on Dec. 3, 2014.

(51) Int. Cl.
| | | |
|---|---|---|
| *B01D 45/00* | (2006.01) | |
| *G01N 1/22* | (2006.01) | |
| *B01D 45/16* | (2006.01) | |
| *B01D 46/00* | (2006.01) | |
| *B01D 50/00* | (2006.01) | |

(Continued)

(52) U.S. Cl.
CPC ........... *G01N 1/2211* (2013.01); *B01D 45/16* (2013.01); *B01D 46/0031* (2013.01); *B01D 50/002* (2013.01); *G01N 1/2205* (2013.01); *G01N 1/2247* (2013.01); *B01D 17/0208* (2013.01); *B01D 17/0214* (2013.01); *B01D 17/045* (2013.01); *B01D 17/10* (2013.01);
(Continued)

(58) Field of Classification Search
CPC .. G01N 1/2211; G01N 1/2247; G01N 1/2205; G01N 1/2035; G01N 2035/00326; B01D 46/0031; B01D 45/16; B01D 50/002; B01D 17/0208; B01D 17/0214; B01D 17/045; B01D 17/10; Y10T 137/0396; Y10T 137/598
See application file for complete search history.

(56) References Cited

U.S. PATENT DOCUMENTS

| | | | | |
|---|---|---|---|---|
| 2,999,563 | A | * | 9/1961 | Wehn .................... B01D 50/002 55/293 |
| 3,014,553 | A | | 12/1961 | Jerman |

(Continued)

OTHER PUBLICATIONS

Author Unknown, Cyclonic Separation, Wikipedia, Oct. 15, 2014 https://en.wikipedia.org/wiki/Cyclonic_separation.

(Continued)

*Primary Examiner* — Dung H Bui
(74) *Attorney, Agent, or Firm* — Joseph T Regard, Ltd plc

(57) ABSTRACT

A cyclonic filter separator with liquid block capabilities formed to separate liquids in a fluid stream for on-stream and spot sampling of natural gas or the like, particularly pressurized process gas having liquid entrained therein, otherwise referenced as multiphase or "wet". The present invention incorporates a liquid block apparatus downstream the cyclonic separator to provide to further prevent liquid passing therethrough, ensuring a dry gas sample stream for analysis or the like. A coalescing membrane may be situated intermediate the cyclonic separator and the liquid block, which coalescing membrane may further be linked to the liquid block such that differential pressure associated with the operative state of the membrane causes the liquid block to engage, blocking the flow of fluid therethrough.

19 Claims, 7 Drawing Sheets

Figures 1A, 1B:
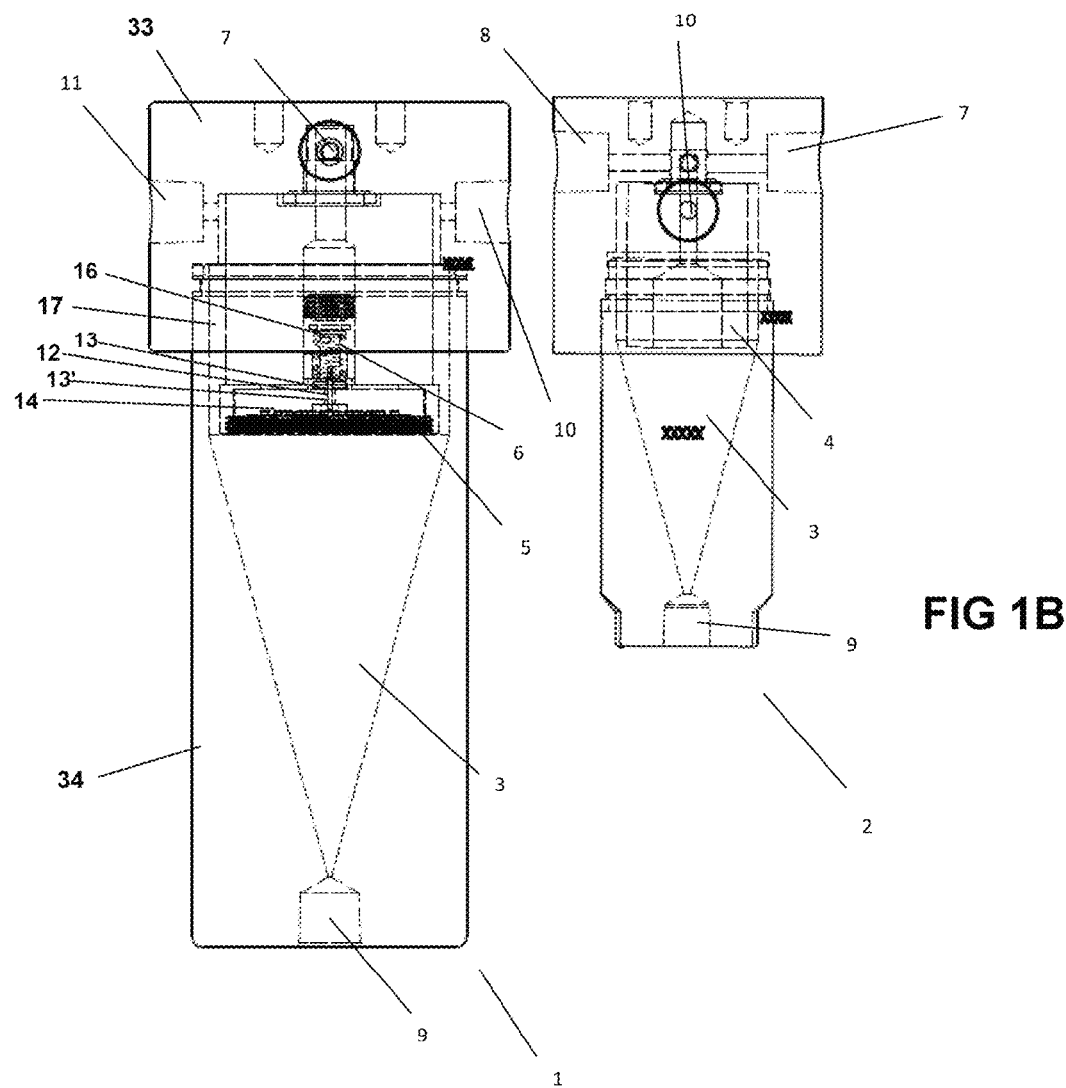

(51) Int. Cl.
   *B01D 17/02* (2006.01)
   *B01D 17/04* (2006.01)
   *B01D 17/00* (2006.01)
   *G01N 1/20* (2006.01)
   *G01N 35/00* (2006.01)

(52) U.S. Cl.
   CPC . *G01N 1/2035* (2013.01); *G01N 2035/00326* (2013.01); *Y10T 137/0396* (2015.04); *Y10T 137/598* (2015.04)

(56) References Cited

U.S. PATENT DOCUMENTS

| | | | |
|---|---|---|---|
| 3,471,775 A | 10/1969 | Birnstingl | |
| 3,581,476 A | 6/1971 | Donnelly | |
| 3,778,977 A | 12/1973 | Conn | |
| 3,831,452 A | 8/1974 | Pittenger | |
| 4,481,833 A | 11/1984 | Bajek | |
| 4,497,714 A | 2/1985 | Harris | |
| 4,586,390 A | 5/1986 | Helke | |
| 4,624,779 A | 11/1986 | Hurner | |
| 4,836,305 A * | 6/1989 | Curlett | E21B 17/003 175/215 |
| 4,838,906 A | 6/1989 | Kiselev | |
| 5,237,881 A | 8/1993 | Ross | |
| 5,579,803 A | 12/1996 | Welker | |
| 5,698,014 A | 12/1997 | Cadle | |
| 5,755,965 A | 5/1998 | Reiber | |
| 5,777,241 A | 7/1998 | Evenson | |
| 6,003,362 A | 12/1999 | Dieckmann | |
| 6,210,575 B1 | 4/2001 | Chase et al. | |
| 6,284,547 B1 | 9/2001 | Schafer | |
| 6,332,356 B1 | 12/2001 | Hecht | |
| 6,357,304 B1 | 3/2002 | Mayeaux | |
| 6,701,794 B2 | 3/2004 | Mayeaux | |
| 6,764,536 B2 | 7/2004 | Welker | |
| 6,818,045 B2 | 11/2004 | Welker | |
| 6,851,309 B2 | 2/2005 | Lenzing | |
| 6,904,816 B2 | 6/2005 | Mayeaux | |
| 7,004,041 B2 | 2/2006 | Mayeaux | |
| 7,097,693 B1 | 8/2006 | Mayeaux | |
| 7,134,318 B2 | 11/2006 | Mayeaux | |
| 7,337,683 B2 | 3/2008 | DeFriez et al. | |
| 7,907,693 B2 | 3/2011 | Bae et al. | |
| 8,087,308 B2 | 1/2012 | Gauthier et al. | |
| 8,176,766 B1 | 5/2012 | Ruiz | |
| 8,424,396 B2 | 4/2013 | Knight | |
| 2001/0015093 A1 | 8/2001 | Kempe | |
| 2002/0036167 A1 | 3/2002 | Mayeaux | |
| 2003/0172632 A1* | 9/2003 | Matsubara | B01D 45/16 55/417 |
| 2005/0223829 A1 | 10/2005 | Mayeaux | |
| 2007/0068223 A1 | 3/2007 | Chen | |
| 2007/0128079 A1 | 6/2007 | Counts | |
| 2008/0092734 A1* | 4/2008 | Benner | B01D 45/16 95/26 |
| 2008/0307901 A1 | 12/2008 | Knight | |
| 2009/0107532 A1 | 4/2009 | Lonne | |
| 2011/0185892 A1 | 8/2011 | Smith | |
| 2011/0308311 A1 | 12/2011 | Dalla Betta | |
| 2012/0000366 A1 | 1/2012 | Mixdorff | |
| 2014/0076027 A1 | 3/2014 | Nicholson | |
| 2015/0377750 A1 | 12/2015 | Scipolo et al. | |

OTHER PUBLICATIONS

Collins Products Co, Collins Products Company Catalog, date uncertain (boliovod 2008), pp. 31.
Collins Products Co, Collins products Company website image, 2014, www.collins-products.com.
A+ Corp, Tornado 602 Brochure, 2012.
Dekati Ltd of Finland, Dekati Cydone product brochure, Aug. 2014, origin unknown.

* cited by examiner

CYCLONIC SYSTEM FOR ENHANCED SEPARATION OF FLUID SAMPLES AND THE LIKE, AND METHOD THEREFORE

BENEFIT CLAIM

The present application claims the benefit of U.S. Provisional patent Application Ser. No. 62/087,067 filed Dec. 3, 2014, listing as inventor Valmond Joseph St Amant III, entitled "Cyclonic System for Enhanced Separation of Fluid Samples and the Like".

FIELD OF THE INVENTION

The invention relates to sampling of pressurized process fluids for on-stream and spot sampling of pressurized process fluid such as natural gas or the like having liquid entrained therein, or otherwise referenced as multiphase or "wet". The present invention contemplates a cyclonic filtration system formed to separate and exclude entrained liquids in the process gas stream, preventing same from entering the sample stream. The preferred embodiment of the invention contemplates the added feature of an coalescing element and liquid block feature to provide a safeguard to exclude any liquid, so as to provide a dry gas sample stream for analysis or the like.

BACKGROUND OF THE INVENTION

Natural gas is bought and sold based on its heating value. It is the BTU content that determines the monetary value of a given volume of natural gas. This BTU value is generally expressed in decatherms (one million BTU). In the determination of total heat value of a given volume of gas, a sample of the gas is analyzed and from the composition its heat value per unit volume is calculated. This value is generally expressed in BTU/cu ft. The typical range of transmission quality gas ranges between 1000 and 1100 BTU/cu ft. Production gas, storage facility gas, NGL, and new found Shale Gas can have much higher heating values up to or even exceeding 1500 BTU/cu ft.

There has been a long standing controversy between gas producers and gas transporters regarding entrained liquid typically present in most high BTU/cu ft. gas (rich or "wet" gas).

Transporter tariffs require essentially liquid-free gas. Hydrocarbon liquid in the gas being transported causes operational and safety problems. The practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained hydrocarbon in any form.

Therefore, to fully comply with the current industry standards, there exists a compelling need to effectively prevent entrained liquids from entering sample systems. Membrane-tipped probes such as the A+ Corporation Genie Probe (see U.S. Pat. No. 6,357,304, U.S. Pat. No. 6,701,794, U.S. Pat. No. 6,904,816, U.S. Pat. No. 7,004,041, and U.S. Pat. No. 7,134,318) have been used for many years to shed entrained liquids inside pressurized pipelines. However, these systems can be overwhelmed with excessive liquid loading, causing the maximum allowable differential pressure to be exceeded, which may force liquids through the coalescing elements, and into the sample system.

The differential pressure needed to force liquids through the coalescing elements is a function of the surface tension of the liquid as well as the construction of the coalescing element. This can be further complicated by the use of various liquid chemicals, which are routinely injected into the process, gas such as corrosion inhibitors, amine and carbon dioxide inhibitors, as well as chemicals meant to dry the gas, like alcohols and glycols.

These liquid chemicals may have low surface tensions and may penetrate coalescing elements, in which case said liquid chemicals may combine with the sample, or lower the surface tension of entrained liquids at the coalescing membrane, making it easier for the said undesired liquids to penetrate and get past some coalescing elements. Also, some coalescing elements may have temperature limitations, and thus may be impractical for some applications.

Further, coalescing membranes or the like may have to be changed periodically as a maintenance precaution to insure reliable operation. Accordingly there is a need for a physical pre-filter to eliminate the bulk of the liquid entrained in the gas which would operate in a variety of conditions with little maintenance, and which is more reliable in operation than current systems.

Cyclonic separation techniques have been utilized in a variety of capacities for over 100 years. A typical cyclonic separator channels a fluid stream through a housing having a geometry formed to generate a vortex, exploiting centrifugal force with gravity and pressure differentials to separate liquid particles from gaseous streams, as well as other applications.

Cyclone-type pre-filters have been used for many decades. For example, D. W. Birnstingl describes a measuring head for a conductivity meter combining a conductivity cell with a cyclone filter to filter liquid in U.S. Pat. No. 3,471,775 filed in 1966.

UOP Inc. of Des Plains, Ill., describes a sampling probe that uses a V-shaped shield to pre-filter particles from sample (see U.S. Pat. No. 4,481,833 from 1984). Another company, Anarad Inc. of Santa Barbara, Calif., describes a filter probe for stack gas that uses an inertial filter with a constant bypass flow requirement to remove dust without clogging (U.S. Pat. No. 5,237,881 from 1993). The University of Akron describes a cyclone collection vessel combined with filter media for separation of a suspension (U.S. Pat. No. 6,210,575 from 2001). M & C Products Analysis Technology, Inc. of Ventura, Calif., describes an in situ particle separation system with filter media for separating particles from gas samples (U.S. Pat. No. 7,337,683 from 2008).

More recently, the General Electric Company of Schenectady, N.Y. describes sample probe for removing particles from a gas stream using a shield and a flow reversal technique (U.S. Pat. No. 8,087,308 from 2012). These devices are not used to remove entrained liquids from gas samples. A far as this applicant is aware, no one in industry has contemplated using the cyclone technology to solve the problem of entrained liquids in natural gas for sampling.

Dekati Ltd of Finland offers the CYCLONE brand cyclonic separator for removal of large particles from a Sample Stream. This device is designed to be placed in a flue gas flow in a stack as well as exterior to the stack. In either instance, an isokinetic sampling probe is utilized to draw the sample. Various isokinetic nozzles are available and may be utilized interchangeably, depending upon the circumstances of use.

Other types of fluid separators may include:

Filter Vane Separators utilize a structure comprising a series of plates or baffles along a passageway to exploit inertial impaction of the fluids, combined with gravity, to facilitate separation.

Centrifugal separators which utilize centrifugal forces to separate the heavier fluid droplets or particles from the gas stream. Cyclone separators operate on this principal as well as well as knock-out drums.

Liquid/Gas coalescer cartridges, filters, membranes and the like are generally not suitable for removal of liquids in bulk, relying upon inertial impaction, the particles engaging a fibrous mass in a container which may include an indirect pathway utilizing inertial impaction and gravity to collect and drain fluid.

Mist Eliminators likewise rely upon the principal of inertial impaction, but instead of plates or baffles, relying upon fibers, meshes or the like.

A+ Corporation makes a self-cleaning filter under the trademark TORNADO (for example, model 602). It is an external filter having self-cleaning tornado action using a single element, multi-layer stainless steel filter media. Another external cyclonic filter is made by Collins Products Co, maker of the SWIRLKLEAN brand bypass filter which uses a cyclone-type filter external to the pipeline, situated upstream the analyzer, although the SWIRLKLEAN system does not utilize gravity separation, instead exploiting a bypass technique as detailed at http://www.collins-products.com/.

To summarize, the prior art teaches various systems for removing liquid particulates or the like from a gaseous fluid stream. Removal of such entrained liquid is imperative as a component of gas analysis as detailed above, although such systems are imperfect and many designs can be overwhelmed by a liquid slug or the like. Anytime liquid is removed from the source and transported into the sample system, the liquid distorts the true composition of the sample.

However, due to shortcomings in the above systems there remains a long felt, but unresolved need for a system with the ability to reliably prevent liquids from overwhelming the separator, thus preventing sample distortion and contamination, which can equate to wrong analysis and very costly incorrect monetary exchanges.

It would therefore be an improvement over the art to provide a cyclonic separator system for removing liquid from fluid sample flow which may not rely solely upon a conventional membrane or filter, and overall requires less maintenance than the prior art systems currently available.

GENERAL SUMMARY DISCUSSION OF THE INVENTION

Unlike the known prior art systems, the device of the present invention provides an effective liquid separator/filter which relies upon a more robust cyclonic separator technique, which may or may not include a membrane or filter separator downstream therefrom. The system as shown is compact and sturdy, while preferably situated external the process flow stream, its compact size allows use in a variety of applications, and may include insertion into the pressurized pipeline to operate at the prevailing pressure and temperature, under certain circumstances.

The preferred embodiment of the present invention contemplates a unique cyclonic separator having a fluid separation membrane or filter downstream therefrom, with a liquid block apparatus downstream the fluid separation membrane/filter, providing triple liquid exclusion redundancy and insuring that no fluid is present in the sample flow entering the analyzer/sampling apparatus, and that the sample gas leaving the system is "dry".

The preferred embodiment of the present invention thereby provides a redundant system for preventing entrained liquid from entering the sample stream to the analyzer while ensuring that a single gas-phase sample is taken.

Alternatively, an alternative embodiment provides the cyclonic separator with the liquid block device and no membrane/filter therebetween, substantially increasing operation time between maintenance requirements and no need for membrane/filter changes, albeit without the triple redundancy of the preferred embodiment, so this system is envisioned as being more suitable for less "wet" fluid streams.

In either embodiment, the present invention reduces or may even eliminate the need for filter elements that must be replaced or cleaned. It protects the entire sample system from contamination that otherwise would require costly downtime for cleaning or replacement. By preventing undesired liquids from entering the sample, the present lessens the likelihood of sample distortion and flawed analysis, especially when utilizing the current API and GPA sampling standards.

The first, preferred embodiment of the present provides a unique cyclone separator formed to receive fluid flow from an inlet, providing a first stage of liquid separation. The present embodiment then utilizes a coalescing element downstream the cyclone separator/filter, so that the coalescing element coalesces entrained mist or very fine aerosol droplets which might otherwise pass through the cyclone, and thus prevents same from being introduced into the sample system.

Finally, a liquid block device may be provided downstream to prevent passage of liquid therethrough in the event the coalescing element becomes oversaturated with liquid, resulting in excessive pressure differential, or pass-through of low surface tension liquids which might be unaffected by the coalescing element. Thus the preferred, first embodiment provides two stages of liquid separation with the third stage stopping liquid flow as a fail-safe, thereby preventing destructive liquid flow to any analyzer of the like downstream the system, all in an easily maintained unit having a compact footprint.

A second embodiment utilizes the first stage cyclone filter, but without any filter or coalescing element of any type behind the cyclone filter to minimize maintenance requirements, although a liquid block may be provided downstream as required.

The inlet opening size, insertion diameter/clearance, and length and diameter of the conical section, as well as the outlet and drain diameters may need to be properly proportioned to optimize the flow-to-filter ratio of the cyclone filter. This ratio must properly sized, taking into account the normal analytical flow rate in a gas or vapor only single phase sample so that the cyclone filter supplies the appropriate flow of sample. Further, the passageways must also be sized so that when liquid slugs are present, the cyclone filter can remove the liquid prior to entering the sample stream intended for the analyzer.

The coalescing element downstream of the cyclone separator/filter could be sintered plastic, or metal, spun borosilicate glass, membrane material, etc. Still another embodiment teaches various configuration inserts for affecting/optimizing flow within the separator, utilizing a diverse pathway, baffles, etc to hinder the free passage of fluid particulates therethrough.

Lastly, various other elements such as pressure reducer(s), etc can be provided downstream or even upstream the separator as necessary and/or desirable.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1A is a side, partially cutaway view of the first, preferred embodiment of the present invention, illustrating a cyclone-type (also referenced as "cyclonic") separator/filter, the present embodiment further illustrating a coalescing element downstream of the cyclonic separator, and a liquid block downstream the coalescing element.

FIG. 1B is a side view of the second, alternative embodiment of the device of FIG. 1A, viewing through inlet 10, the second embodiment provided without the coalescing element or liquid block provided shown in the first embodiment of FIG. 1A.

FIG. 2A is a side view, partially cutaway view of the invention of FIG. 1B, illustrating via arrows fluid flow/liquid separation, and draining port.

FIG. 2B is a side, partially cutaway view of the invention of FIG. 2A showing inlet 10.

FIG. 3 is a side, cutaway view of the first embodiment of FIG. 1A, illustrating fluid flow via inlet, outlet, bypass, and drain.

FIG. 4 illustrates the second embodiment of FIG. 1B, showing threaded connections for the components, and further providing an additional, unique threaded or spiraled exterior of insert 4 to facilitate spiral or cyclonic flow about the insert from inlet to separation funnel/cyclonic chamber 3.

FIG. 5 is a side, partially cutaway view of the invention of FIG. 4, illustrating via phantom internal structure of the various components shown.

FIG. 6 is a side, exploded view illustrating the various components of first, preferred embodiment of the cyclonic device of FIG. 1A, illustrating in phantom the internal structure of same.

FIG. 7 is a side, exploded view of the device of FIG. 1A with the added feature shown of the incorporation of the unique threaded or spiraled exterior of insert utilized with the device to facilitate spiral or cyclonic flow about the insert from inlet to separation funnel/cyclonic chamber 3, the insert further containing a coalescing element 5 and liquid block 6 therein, formed for fluid passage therethrough to outlet 7.

DETAILED DISCUSSION OF THE INVENTION

Referring to the drawings, the present invention comprises a cyclone separator in the form of a separation funnel/cyclone chamber 3 (may also be referenced as cyclone filter) the first embodiment 1 further incorporating a coalescing/membrane filter or element 5 downstream the cyclone chamber 3, so that the coalescing element 5 is situated to receive and capture, via coalescence, entrained mist or very fine aerosol droplets flowing through cyclone chamber 3, the coalescing element formed to capture any remaining aerosol droplets in the fluid stream beyond the cyclone filter, and preventing same from being introduced into the sample stream downstream the coalescing filter.

In both the first 1 and second 2 embodiments of the invention, if a slug of liquid is present in the sample stream entering the cyclone filter, said fluid flow passes through separation funnel/cyclone chamber 3 which can (within limits) separate said slug of liquid (or any residual liquid therefrom) and prevent same from passing through outlet port 7 leading to the sample system.

The cyclonic separator/filter of the present invention comprises a base 33 to which a housing 34 (alternatively referenced as a sleeve) is removably affixed thereto. An outlet 7 is provided (shown formed in base 33) to engage an outflow passage leading to a sample analyzer, container, etc.

Base 33 engages said housing 34 via threaded connection 41 or the like, said housing 34 formed to house insert 4 shown being cylindrical and formed to be enveloped by a cylindrical inner walls 35, 35' formed in base 33 and housing 34, respectively, forming a clearance 17 therebetween for passage therethrough, as will be further discussed herein.

Insert 4 includes an extension 27 emanating therefrom formed to engage the base at receiver 27' so as to provide a passage to outlet 7. The outer surface of extension 27 may be threaded to threadingly engage receiver 27' formed in base. An o-ring or other seal may be provided to sealingly connect the two components and insure a fluid seal therebetween.

Housing 34 may also be threaded at its first end 30 so as to threadingly engage base 33, and a seal such as an O-ring or the like may be provided as required for a fluid-tight connection.

Formed within housing 34 is a conical cavity forming a tunnel/cyclone chamber 3 tapering from its widest point to an end or apex having a drain 9 in the vicinity of the second end 30' of housing.

Continuing with the figures, the present invention is shown having an inlet 10 and bypass 11 port associated with base 33, the inlet formed to receive a process flow or the like via a conduit or such so as to facilitate fluid flow 24 tangentially therein and about the passage formed by clearance 17.

A portion of the fluid flowing via inlet 10 passes through clearance 17 and exits via the bypass 11, the remaining flow 24 spiraling via clearance 17 between insert 4 and inner wall 35, 35' formed by base 33 and housing 34, spirally about and down along the outer surface 19 of insert 4 to the inverted cone-shaped portion forming the separation funnel/cyclone chamber 3, said chamber 3 formed to further facilitate cyclonic action within the chamber forming a vortex 22 to facilitate fluid-liquid separation as the gas of the sample flow is drawn upward 22' through the lower pressure center of the vortex, the liquid is separated via cyclonic action and gravity, and flows to drain 9.

Most or all liquid particulates in the fluid stream are thereby cyclonically extracted from the stream and drain through drain port 9, with any residual liquid taken out by coalescing element 5 downstream therefrom (in the first embodiment 1 of the invention where such element 5 feature is provided).

Note again that the coalescing element 5 may be situated within insert 4 at the mouth of the separation funnel/cyclone chamber 3. The present configuration allows excess liquid coalesced into the membrane to collect and drip back into the funnel/cyclone chamber, where it is separated via the cyclonic action and drained via drain 9.

Further, the described stacking or nesting of the coalescing element 5 within insert 4 in the first embodiment of the invention 1 decreases the amount of space required when compared to prior art systems. In the present system, an exemplary coalescing element may comprise, for example, A+ Manufacturing LLC's AVENGER Brand Coalescing membrane filter Model 33(M) and 38(M).

In addition, in the preferred, first embodiment 1 of the present invention, a liquid block device 6 can be provided downstream and interfacing the coalescing element, shown in the first embodiment 1 situated within insert 4, the liquid block device 6 being configured to activate to prevent passage of liquid therethrough in the event the coalescing element is over-saturated with liquid, resulting in excessive pressure differential, or in the event of pass-through of low surface tension liquids which might be unaffected by the coalescing element.

In the present, first 1 embodiment illustrated embodiment, a liquid block device 6 is provided, the preferred, exemplary embodiment thereof includes a spring 16 biased arm 12 having first 13 and second ends 13', the second end 13' having a seal 23 such as an o-ring associated therewith.

The second end 13' of arm 12 and associated seal 23 is configured to engage membrane retention plate 25 situated on the exit or downstream side 14 of the coalescing element 5. While seal 23 is biased to a default open, flow position, said bias can be overcome to reposition said seal 23 to engage a seat 21 into a sealing position, blocking the outlet flow passage therethrough. Particularly, upon coalescing element 5 becoming oversaturated with fluid, a pressure differential build-up 26 can occur to urge said coalescing element to apply pressure to a retention plate 25 associated with the downstream side of coalescing element 5, which retention plate 25 applies pressure to the second end 13' of arm 12.

Sufficient differential build 26 and associated pressure associated with a clogged coalescing element 5 will overcome the spring bias 16 to urge said seal 23 to engage seat 21 to a sealing position, blocking further flow and thereby preventing liquid from passing therefrom.

Thus, flow is cut off and any sensitive equipment (i.e. analyzer) downstream the system is protected from liquid contamination. Further, the liquid block device would ideally also activate in the event of pass-through of low surface tension liquids which might be unaffected by the coalescing element.

In both the first 1 and second 2 embodiments of the present invention, it is noted that the configuration of the cylindrical insert 4 can vary depending upon the application and associated needs, including, for example, a linear or blade configuration, a triangular or polygonal configuration as well as others, which may be interchangeably changed as the need arises.

To facilitate the desired downwardly descending spiral flow as the fluid flows along from inlet about the outer surface of insert 4, threads 20 can be provided about the outer diameter of the cylinder insert 4. The sizes and scales of the inserts may vary depending upon the application to vary the clearance between said insert and the outer housing, which forms the passage for the fluid stream flowing thereabout and therethrough.

The inlet opening size and the length and diameter of the conical section and internal barrier as well as the outlet and drain diameters may need to be sized for the flow to filter ratio of the cyclone filter/separator. This ratio must be sized correctly so that under normal analytical flow rates in a gas or vapor only single phase sample, the cyclone filter supplies the appropriate flow of sample.

In addition, the passageways must also be sized so that when liquid slugs are present, the cyclone filter can remove the liquid in sample intended for the analyzer. The material of construction of the coalescing element of the first embodiment 1 may be application dependent (i.e. may depend on process fluid, analytical flow rate, the properties of the type of liquid entrained, etc.).

Figures 2A, 2B:
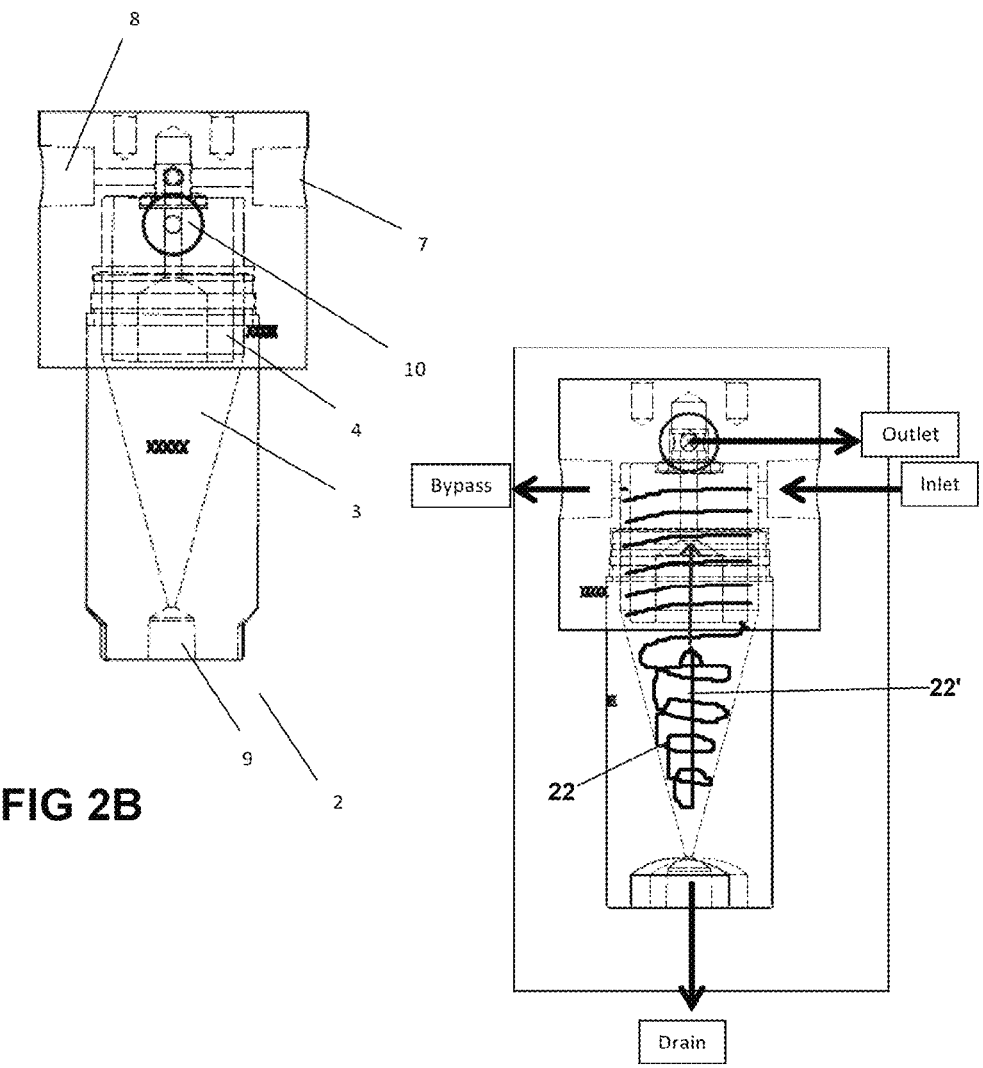
Figure 3:
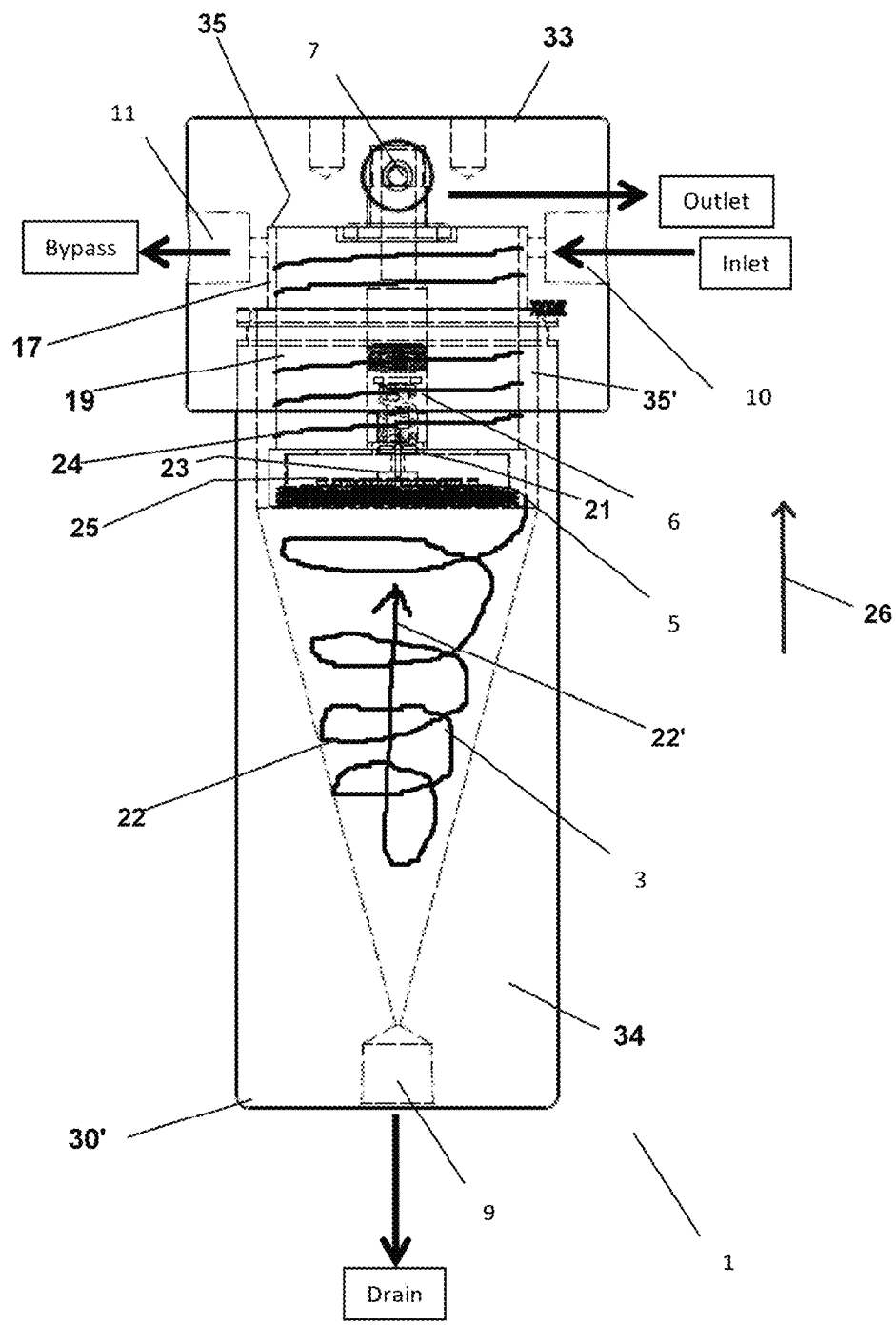
Figure 4:
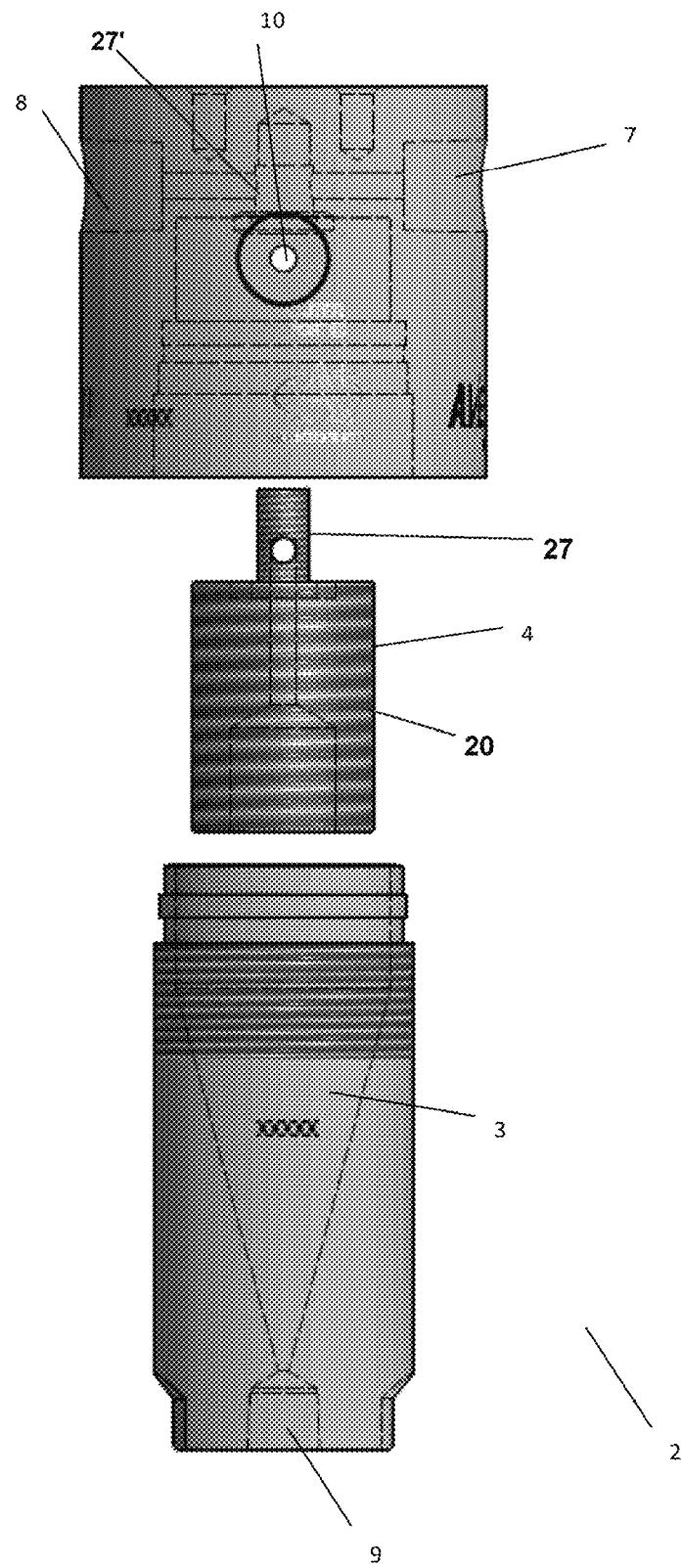
Figure 5:
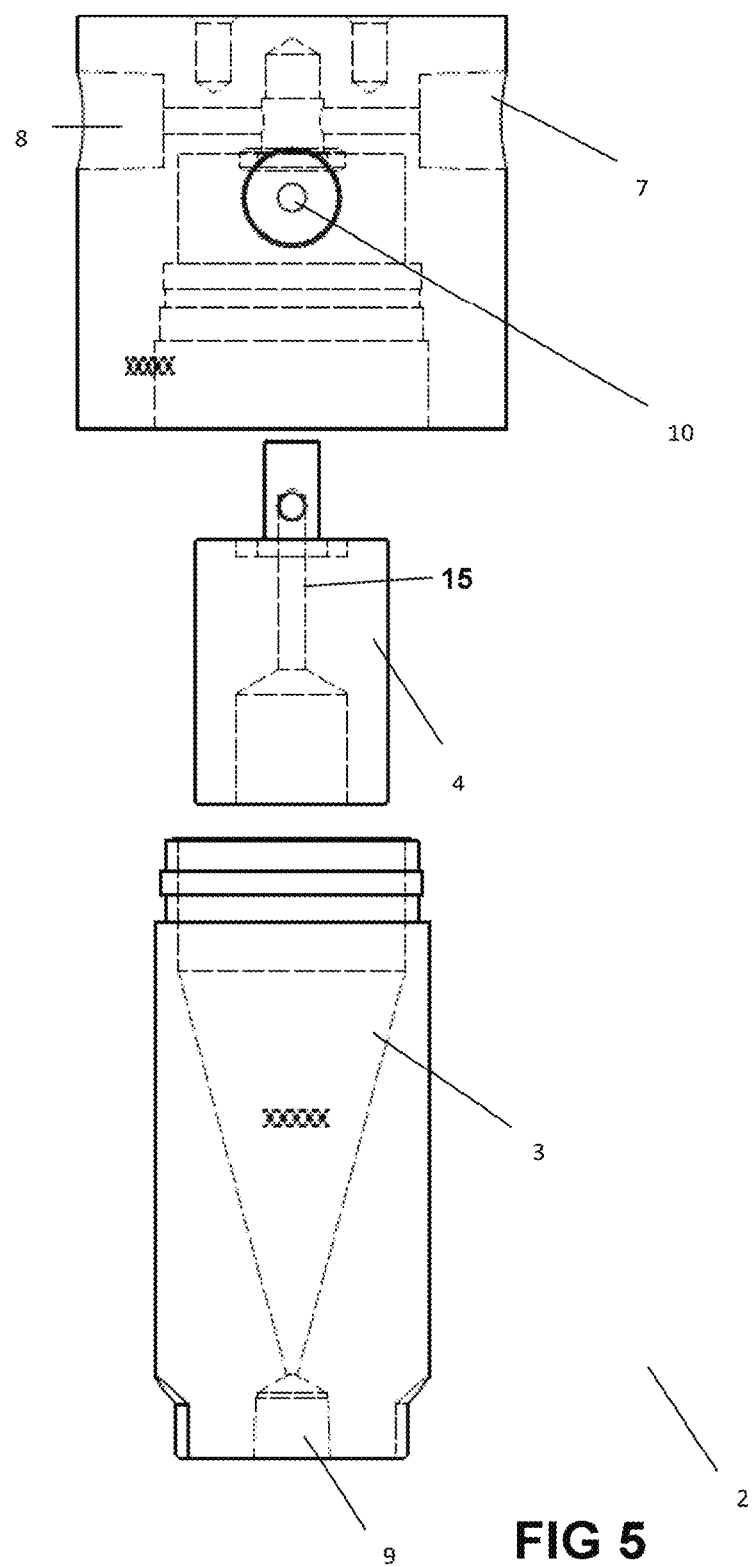
Figure 6:
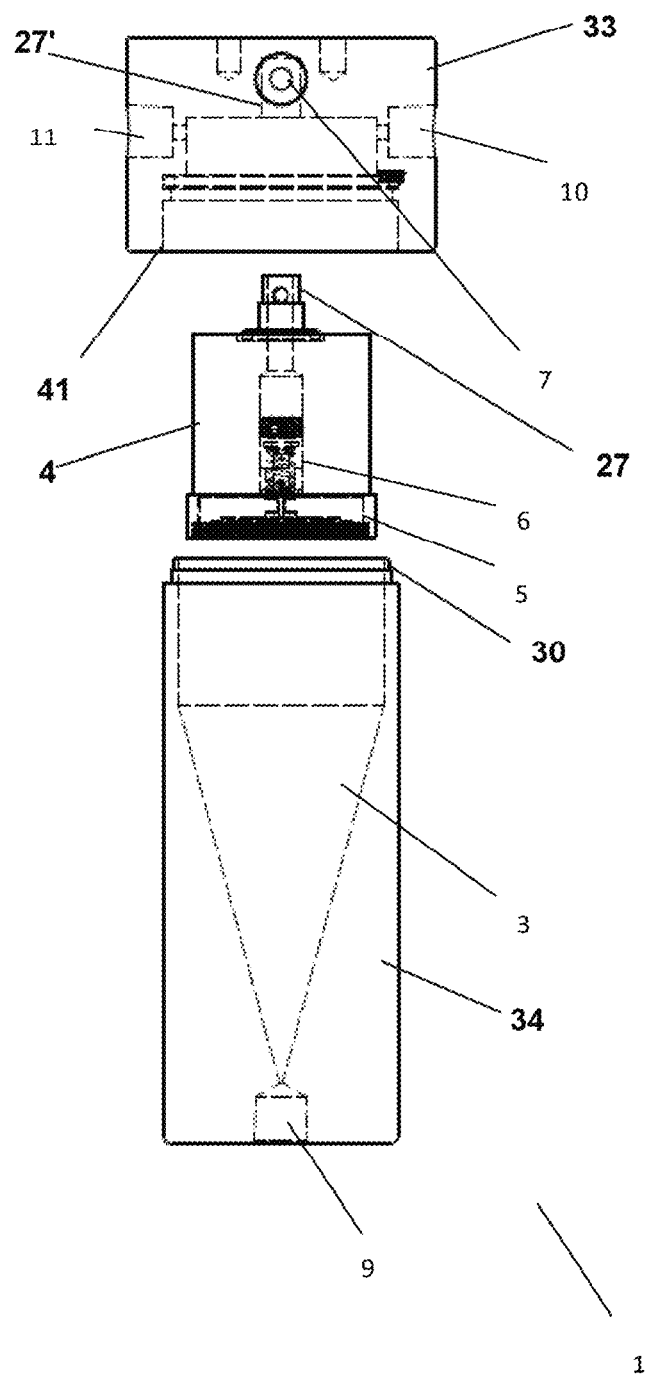
Figure 7:
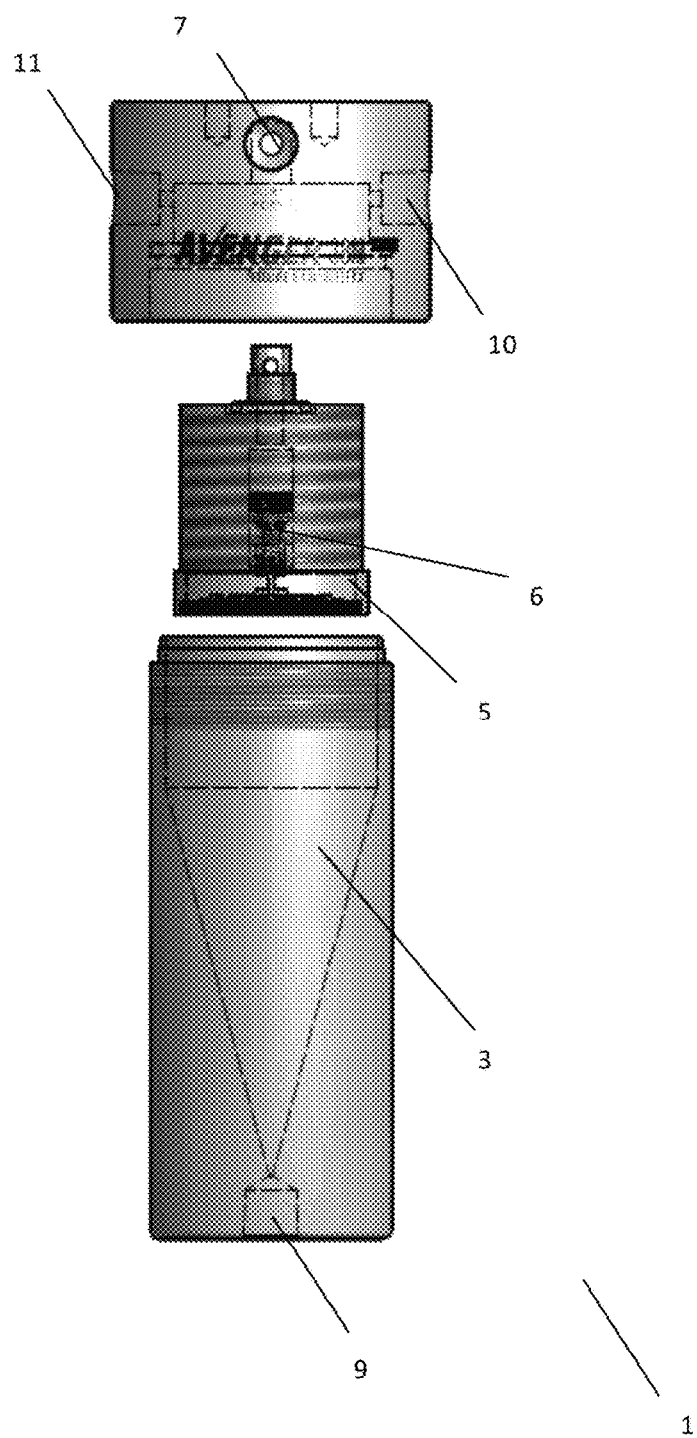

Continuing with FIGS. 1B, 2A-2B, 4 and 5, the second embodiment of the present invention would utilize a cyclone separator/filter formed in a housing engaging a base similar in concept to that taught in the first embodiment, but without the coalescing element (5) or liquid block (6) as shown in the insert of the first embodiment, as such components may only be required when there exists substantial liquid in the flow stream and accordingly would not be provided in the second embodiment. Accordingly, the second embodiment can provide an effective, compact, low maintenance, and reliable liquid filter using cyclonic separation, providing filtered gas therefrom to outlet port 7 in flow streams without excessive liquids present therein and in installations where such separation is compliant with the desired operational specification.

ELEMENTS OF THE INVENTION

1 first embodiment of cyclone separator
2 second embodiment
3 separation funnel/cyclone chamber
4 insert
5 coalescing element/membrane filter
6 liquid block
7 outlet port
8 outlet
9 drain port
10 inlet port
11 bypass port
12 biased arm—liquid block
13,' first, second ends
14 exit side coalescing element
15 passage
16 spring
17 clearance
19 outer surface of insert 4
20 threads
21 seat
22,' vortex, upward
23 seal
24 fluid flow
25 retention plate
26 build up
27,' extension, receiver
29 body
30, 30' first second ends of housing
33 base
34 housing
35,' cylindrical inner walls
41 connection The embodiments listed are not intended to be an exhaustive list of applications for the cyclone filter but only intended to show the need and some of the practical applications of the invention. Further, the invention embodiments herein described are done so in detail for exemplary purposes only, and may be subject to many different variations in design, structure, application and operation methodology.

Thus, the detailed disclosures therein should be interpreted in an illustrative, exemplary manner, and not in a limited sense.

I claim:

1. A device for sampling a fluid in a fluid stream, comprising:
   a base having an inlet formed to receive said fluid stream;
   a housing having first and second ends, said first end formed to engage said base, said housing containing a cyclonic separator comprising a lower, conical cyclone chamber associated with said second end of said housing, said cyclone chamber having an internal geometry formed to facilitate a cyclone to separate liquid from said fluid stream, providing a treated fluid stream, and a liquid drain;
   an insert having a central cavity forming a passage to said base and a cylindrical outer surface, said outer surface formed to engage said fluid stream so as to direct same to said cyclone chamber, said insert formed to receive said treated fluid stream and direct same to an outlet;
   said housing having a cylindrical cavity formed therein having an inner diameter formed to envelope the outer surface of said insert so as to form a clearance therebetween to form a fluid passage to receive fluid flow from said base to said cyclone chamber;
   a coalescing element situated downstream said cyclone chamber;
   a liquid block mounted downstream said coalescing element, said liquid block comprising a spring-biased arm having a seal, said seal formed to engage a retention plate associated with said coalescing element whereby, upon a said coalescing element becoming saturated with fluid, a pressure differential is created to urge said seal to engage a seat, so as to prevent the flow of said liquid therethrough.

2. The device of claim 1, wherein said housing is threadingly affixed to said base.

3. The device of claim 1, wherein there is provided a pressure reducer downstream said coalescing element.

4. The device of claim 1, wherein said seal comprises gasket material.

5. The device of claim 1, wherein said seal comprises an o-ring.

6. The device of claim 1, wherein said fluid stream is directed from a process gas stream in a pipeline, said device being situated exterior said pipeline.

7. The device of claim 1, wherein said internal geometry of said cyclone chamber is in the form of an inverted frustoconical chamber.

8. The device of claim 1, wherein said coalescing element comprises a membrane.

9. The device of claim 8, wherein said coalescing element is situated in said central cavity of said insert.

10. The device of claim 1, wherein said liquid block device operatively engages said coalescing element via said spring biased arm.

11. A method of separating a gas from a fluid stream, comprising the steps of:
   a. providing a device comprising:
   ai. a base having an inlet formed to receive said fluid stream;
   aii. a housing having first and second ends, said first end formed to engage said base, said housing containing a lower, conical cyclone chamber associated with said second end of said housing, said cyclone chamber having an internal geometry formed to facilitate a cyclone to separate liquid from said fluid stream, providing a treated fluid stream, and a drain for draining liquid therefrom;
   aiii. an insert having a central cavity forming a passage to said base, and a cylindrical outer surface, said outer surface formed to engage said fluid stream so as to direct same to said cyclone chamber, said insert formed to receive said treated fluid stream and direct same to an outlet;
   aiv. said housing having a cylindrical cavity formed therein having an inner diameter formed to envelope the outer surface of said insert so as to form a clearance therebetween to form a fluid passage to receive fluid flow and direct same from said base to said cyclone chamber;
   av. a coalescing element situated downstream said cyclone chamber;
   avi. a liquid block mounted downstream said coalescing element, said liquid block comprising a spring biased arm having a seal formed to engage a retention plate associated with said coalescing element whereby, upon a said coalescing element becoming saturated with fluid, a pressure differential is created to facilitate the positioning of said seal to engage a seat to selectively prevent the flow of said liquid therethrough;
   b. engaging said insert to said base;
   c. engaging said housing to said base so that said housing envelopes at least a portion of said insert, forming a clearance between said outer surface of said insert and said housing;
   d. flowing a fluid stream comprising gas having liquid therein from said base, about said insert via said clearance between said insert outer surface and said housing, to said cyclone chamber,
   e. allowing said internal geometry of said cyclonic chamber to facilitate formation of a cyclone therein;
   f. using said cyclone to facilitate separation of liquid from said fluid stream;
   g. draining said liquid, while facilitating the passage of gas therethrough.

12. The method of claim 11, wherein in step "g" said liquid comprises a liquid slug.

13. The method of claim 12, wherein following step "g" there is provided the added step "h" of flowing said gas through said coalescing element, capturing any entrained liquid therein, providing dry gas.

14. The method of claim 13, wherein following step "h" there is provided the added step "I." of utilizing said coalescing element to close said liquid block upon said coalescing element becoming saturated with liquid.

15. A method of sampling a gas stream having entrained liquid therein, comprising the steps of:
   a. providing a device comprising:
   ai. a base having an inlet formed to receive a fluid stream;
   aii. a housing having first and second ends, said first end formed to engage said base, and a lower, conical cyclone chamber associated with said second end of said housing, said cyclone chamber having an internal geometry formed to facilitate a cyclone to separate liquid from said fluid stream, providing a treated fluid stream, and a drain for draining separated liquid therefrom;
   aiii. an insert having a central cavity forming a passage to said base, and a cylindrical outer surface, said outer surface formed to engage said fluid stream so as to direct same to said cyclone chamber, said insert formed to receive said treated fluid stream and direct same to an outlet;

aiv. said housing having a cylindrical cavity formed therein having an inner diameter formed to envelope the outer surface of said insert so as to form a clearance therebetween to form a fluid passage to receive fluid flow and direct same from said base to said cyclone chamber;

av. a coalescing element situated downstream said cyclone chamber;

avi. a liquid block mounted downstream said coalescing element, said liquid block comprising a spring biased arm having a seal formed to engage a retention plate associated with said coalescing element whereby, upon a said coalescing element becoming saturated with fluid, a pressure differential is created to facilitate the positioning of said seal to engage a seat to selectively prevent the flow of said liquid therethrough;

b. engaging said insert to said base;

c. engaging said housing to said base so that said housing envelopes at least a portion of said insert, forming a clearance between said outer surface of said insert and said housing;

d. receiving a flow of a said gas stream having entrained liquid into said base, providing a sample flow;

e. directing a portion of said sample flow about said outer surface of said insert via said clearance to said cyclone chamber;

f. allowing said sample flow to interact with said cyclonic chamber to form a cyclone;

g. using said cyclone to separate liquid from said sample flow, providing a separated sample flow;

h. draining said liquid into said process gas stream.

16. The method of claim 15, wherein there is further provided after step "h" the added step "I" of flowing said separated sample flow through said coalescing element, separating entrained liquid from said separated sample flow, and draining said liquid via said drain associated with said cyclone chamber, providing dry sample flow.

17. The method of claim 16, wherein there is further provided after step "I" the added step "j" of flowing said dry sample flow through said liquid block.

18. The method of claim 17, wherein there is further provided after step "j" the added step of utilizing said coalescing element to actuate said liquid block, sealing said liquid block, upon said coalescing element becoming saturated with liquid.

19. The method of claim 17, wherein there is further provided after step "I" the added step "j" of flowing said dry sample flow out of said insert, through said base to an analyzer.

* * * * *